United States Patent [19]
Seeliger et al.

[11] Patent Number: 6,140,428
[45] Date of Patent: Oct. 31, 2000

[54] SIMULTANEOUS PRODUCTION OF DICARBOXYLIC ACIDS AND DIAMINES BY SPLITTING POLYAMIDES INTO THEIR MONOMERIC CONSTITUENTS

[75] Inventors: Ursula Seeliger, Ludwigshafen; Wolfgang F. Mueller, Neustadt; Frank Heimann, Ludwigshafen; Guenther Huber, Dannastadt-Schauernheim; Wolfgang Habermann, Mainz; Hartwig Voss, Frankenthal; Hardo Siegel, Speyer, all of Germany

[73] Assignee: BASF Aktiengesellschaft, Ludwigshafen, Germany

[21] Appl. No.: 08/711,995

[22] Filed: Sep. 10, 1996

Related U.S. Application Data

[63] Continuation of application No. 08/351,424, Dec. 12, 1994, abandoned.

[30] Foreign Application Priority Data

Jun. 17, 1992 [DE] Germany .............................. 42 19 756

[51] Int. Cl.⁷ ...................................................... C25B 3/00
[52] U.S. Cl. ........................... 525/418; 204/165; 204/544
[58] Field of Search ............................. 525/418; 204/165, 204/544

[56] References Cited

U.S. PATENT DOCUMENTS

| | | |
|---|---|---|
| 2,840,606 | 6/1958 | Miller . |
| 2,921,005 | 1/1960 | Bodamer . |
| 4,781,809 | 11/1988 | Falcone, Jr. . |
| 5,034,105 | 7/1991 | Berglund et al. .................... 204/182.4 |

FOREIGN PATENT DOCUMENTS

| | | |
|---|---|---|
| 2038830 | 9/1991 | Canada . |
| 438 369 | 7/1991 | European Pat. Off. . |
| 449 071 | 10/1991 | European Pat. Off. . |
| 926 873 | 10/1917 | France . |
| 1 070 841 | 8/1954 | France . |
| 1 088 063 | 9/1960 | Germany . |
| 25 47 101 | 5/1976 | Germany . |
| 39 26 634 | 2/1990 | Germany . |
| 39 26 642 | 3/1990 | Germany . |
| 553 182 | 12/1956 | Italy . |
| 412 922 | 9/1962 | Switzerland . |
| WO 92/05863 | 4/1992 | WIPO . |

OTHER PUBLICATIONS

Habermann et al, WPIDS AN 94–000486 abstracting DE 4219757, Dec. 23, 1993.
Chemical Abstracts, vol. 53, No. 2, Jan. 25, 1960, Ab 14588 (Abstract of Italian 553, 182).

*Primary Examiner*—Jeffrey Mullis
*Attorney, Agent, or Firm*—Keil & Weinkauf

[57] ABSTRACT

A process for the simultaneous production of dicarboxylic acids and diamines from
- a) polymers based on polyamides of dicarboxylic acids or their derivatives with diamines, or
- b) compositions containing essentially such polymers, by splitting these polymers into their monomeric constituents, comprises treating these polymers or compounds with a base in alcoholic medium, and subsequently converting the resulting dicarboxylate salts electrochemically into the corresponding dicarboxylic acids and bases.

5 Claims, 3 Drawing Sheets

SIMULTANEOUS PRODUCTION OF DICARBOXYLIC ACIDS AND DIAMINES BY SPLITTING POLYAMIDES INTO THEIR MONOMERIC CONSTITUENTS

This application is a continuation of application Ser. No. 08,351,424, filed on Dec. 12, 1994 now abandoned.

The present invention relates to a process for the simultaneous production of dicarboxylic acids and diamines from
   a) polymers based on polyamides of dicarboxylic acids or their derivatives with diamines, or
   b) compositions containing essentially such polymers, by splitting these polymers into their monomeric constituents.

The splitting of polyamides such as nylon 66 (polyhexamethyleneadipamide, PA 66) into their monomeric constituents can be carried out in a neutral or acid medium but in general it is preferably carried out in a basic medium, inter alia because of the shorter reaction time.

FR-A-926 873 describes the splitting of polyamides such as PA 66 and PA 610 with inorganic bases, for example with a from 10 to 15% strength by weight alkali metal hydroxide solution such as sodium hydroxide solution, at 200° C. and about 15 bar. The resulting diamine is then extracted or distilled out of the reaction mixture and further purified by vacuum distillation. According to this reference, the free dicarboxylic acid is obtained by addition of a strong acid such as hydrochloric acid to the diamine-free reaction mixture and subsequent precipitation.

In IT-A-553 182 an excess of 20% strength by weight of sodium hydroxide solution at 220° C. and 25 bar reduces the reaction time compared with the process of FR-A-926 873. The diamine is extracted from the aqueous solution with n-butanol. One example concerns the removal of insoluble titanium dioxide, previously present in the polymer in the form of fibers, by filtration after breaking down. The dicarboxylic acid is likewise freed by addition of a strong mineral acid.

FR-A-1 070 841 describes the splitting of PA 66 with alkali metal or alkaline earth metal hydroxide solutions. According to this reference, the reaction mixture is initially worked up by acidifying with sulfuric acid and then the precipitated adipic acid is separated off. Thereafter the filtrate is admixed with potassium hydroxide solution, and hexamethylenediamine separates as an oily layer which can be separated off and purified. This reference also describes the splitting and workup of polymers and copolymers that contain polycaprolactam (PA 6).

DE-A-1 088 063 describes the splitting of PA 66 in a 10% strength by weight methanol NaOH solution. The disodium adipate obtained is converted into the free acid by acidification, while hexamethylenediamine (HMD) can be obtained in pure form by distillation.

U.S. Pat. No. 2,840,606 describes the splitting of PA 66 into disodium adipate and HMD in a two-phase $C_3$–$C_8$-alkanol/water mixture. According to this teaching, the HMD is isolated from the alcohol phase by distillation. The adipic acid is obtained by acidifying the aqueous phase with sulfuric acid and may be purified by crystallization.

DE-A 39 26 642 describes a process and an apparatus based on a four-compartment electrolysis cell for obtaining an acid from its salt. However, no mention is made of reaction parameters and examples in DE-A 39 26 642.

A feature common to all these processes is the isolation of adipic acid through acidification of the respective alkali metal or alkaline earth metal salt solutions. The inevitable inorganic salt by-product, usually sodium chloride or sodium sulfate, not only interferes with the attempt to purify the dicarboxylic acid by crystallization, since it inhibits the latter, but also constitutes a considerable disposal problem.

A further disadvantage is that the processes described cannot be suitably employed for working up technical, for example fiber-reinforced, mineral-filled and/or impact-modified, molding compositions that contain PA 66, since the various additives would disrupt the smooth running of the processes in question.

It is an object of the present invention to provide a process for the simultaneous production of dicarboxylic acids and diamines that is free of the abovementioned disadvantages.

We have found that this object is achieved by a process for the simultaneous production of dicarboxylic acids and diamines from
   a) polymers based on polyamides of dicarboxylic acids or their derivatives with diamines, or
   b) compositions containing essentially such polymers, by splitting these polymers into their monomeric constituents, which comprises treating these polymers or compounds with a base in alcoholic medium and subsequently converting the resulting dicarboxylate salts electrochemically into the corresponding dicarboxylic acids and bases.

Suitable polymers based on polyamides of dicarboxylic acids or their derivatives, for example the corresponding acid halides, preferably the acid chlorides, with diamines are from observations to date polyhexamethyleneadipamide, polyhexamethylenesebacamide and polytetramethyleneadipamide, preferably polyhexamethyleneadipamide.

Suitable compositions containing essentially such polymers, ie. at least 50% by weight of such polymers, also include for example copolyamides with PA 66 and also PA 66 or copolyamides with PA 66 containing fibers and/or additives.

The bases used for splitting the polymers are in general alkali metal hydroxides such as lithium hydroxide, sodium hydroxide and potassium hydroxide, preferably sodium hydroxide, or mixtures thereof, preferably a mixture of sodium hydroxide and potassium hydroxide.

It is preferable to use from 1.8 to 4.0, preferably from 2.0 to 3.0, equivalents of alkali metal hydroxide per repeat unit of polymer, for example —[—$(CH_2)_4$—CO—NH—$(CH_2)_6$—NH—CO—]— in the case of PA 66. If less than 1.8 equivalents of base are used, the result is in general an undesirably high proportion of oligomer. If more than 4.0 equivalents of base are used per repeat unit, this leads in general, in particular in the case of glass fiber-reinforced and/or mineral-filled polyamide molding compositions, to a high degree of degradation of the glass fibers or of the mineral fillers.

In general, the alkali metal hydroxide is used in the form of a from 5 to 25, preferably from 10 to 15,% strength by weight solution in a $C_1$–$C_4$-alkanol. If desired, instead of one alkanol it is possible to use a mixture of different alkanols or an alkanol-water mixture which contains from 0 to 50, preferably from 5 to 40, particularly preferably from 10 to 30, % by weight of water.

The $C_1$–$C_4$-alkanols used can be in general methanol, ethanol, n-propanol, isopropanol, n-butanol, preferably methanol, ethanol and isopropanol.

The reaction is in general carried out at a temperature within the range from 100 to 300° C., preferably from 140 to 220° C. The pressure for the reaction is in general within the range from 0.08 to 15 MPa, although it is also possible to employ a pressure outside this range. Preference is given to working under the autogenous pressure.

Owing to the alkali metal hydroxide, the reaction mixture pH is in general greater than 7.

The duration of the reaction depends essentially on the concentrations of the starting material, on the temperature and on the pressure and will in general be within the range from 0.5 to 15, preferably from 1 to 10, h.

The splitting with a base can be carried out continuously or batchwise.

It can be carried out in customary apparatus with or without stirrer, preference being given to using a pressure vessel equipped with a stirrer system that is particularly suitable for solids dispersion, for example a propeller stirrer or a cross-bar stirrer.

In a preferred embodiment, the starting polymer or polyamide-containing compositions are mechanically comminuted to an average particle size from 0.1 to 50, preferably from 1 to 10, mm before splitting. The comminution can be carried out in a commercial mill, for example in a cutting mill, or, preferably, in particular when the compositions used contain hard materials such as metal inserts, for example bolts, in a hammer mill.

Metal parts present in the material thus comminuted can be removed in a drying separation process using an air table, preferably with subsequent induction separation, using for example a free-fall tube separator, for complete removal of the metal parts, or in a wet separation process, for example by means of a hydrocyclone.

In a particularly preferred embodiment, the polymer or composition feedstock is comminuted in a hammer mill to a size of not more than 50 mm in length, any metal parts present are separated off, and the millbase freed of metal parts is then comminuted to a size within the range from 5 to 12 mm in a cutting mill. If desired, the polymer or polymer-containing composition thus pretreated can then be additionally washed and dried before it is subjected to splitting with a base.

The reaction mixture obtained on splitting the polyamides consists in general of a liquid phase, which contains the diamine, and a solid phase, which contains the precipitated dicarboxylate salt and insoluble constituents.

According to the invention, the solid phase is then separated from the liquid phase.

Suitable processes for separating off the solid phase are known processes such as filtration, sedimentation or centrifuging.

Examples of insoluble constituents are glass fibers, carbon fibers, carbon black, minerals and rubber and any metals not removed or not completely removed beforehand, unless dissolved by the base.

The removed solid phase may if desired be washed in a further operation preferably with an organic solvent, particularly preferably with a $C_1$–$C_4$-alcohol such as methanol, ethanol, n-propanol, isopropanol or mixtures thereof, or with a mixture of a $C_1$–$C_4$-alcohol containing from 0 to 30% by weight of water, very particularly preferably with the solvent component used in the splitting, particularly preferably in a pure $C_1$–$C_4$-alcohol.

The washing can be carried out for example with the apparatus used for the separation such as a belt filter, a centrifuge, a filter press or a centrifugal disk pressure filter, preferably a centrifuge or a filter press, and/or other apparatus suitable for this purpose such as a decanter. The washing operation is preferably carried out in multiple stages and after each stage the insolubles removed in the wash are preferably intimately mixed with the particular washing medium used in order to minimize the loss of solubles. Particular preference is given to using an apparatus in which insoluble matter can be washed in countercurrent.

In a preferred embodiment, the liquid phase of the as-split reaction mixture can be combined with the liquid phases from the wash operations on the solid phase and used as solvent in the hydrolysis, in which case all or some of the diamine can if desired be removed beforehand. Particular preference is given to recirculating the liquid phases from the wash operations on the solid phase directly into the hydrolysis stage.

In a further preferred embodiment, the diamines obtained after the splitting are preferably separated off after the solid phase has been separated off.

The separation of the diamines from the liquid phase of the reaction mixture obtained in the splitting can be carried out by known processes such as distillation, preferably rectification, or extraction.

In general, the removal of the diamines is preceded by the removal of low boilers, primarily the alcohols or alcohol-water mixtures used as solvents, preferably by distillation. This distillation can be carried out in conventional evaporators, such as thin-film or falling-film evaporators, single- or multi-stagedly, preferably multi-stagedly, or in a rectification column.

The solvent obtained in this removal can be directly used in the splitting of the polymers. However, it can also be freed beforehand, advantageously by means of a rectification, from impurities that interfere with the splitting. It can also be desirable to separate off water in this way in order to obtain in this way a suitable composition for the alcohol-water mixture. The rectification can in general be carried out in conventional apparatus such as tray columns or packed columns with arranged or dumped packing.

The diamines are in general isolated in conventional apparatus, preferably tray columns or packed columns if rectification is employed.

In a preferred embodiment, the diamines are obtained in vapor form as a side takeoff from the stripping portion of the rectification column or, likewise preferably, in liquid form as a side takeoff from the enriching portion of the rectification column. The rectification is in general carried out at from 10 to 100 kPa, preferably from 50 to 80 kPa.

Any diamine still present in the rectification residue can if desired be separated therefrom in a further distillation step, for example using a thin-film evaporator, at from 0.5 to 50, preferably from 2 to 30, kPa, preferably in a force-cleaned paddle-type evaporator, since it makes it possible to remove the nonvaporizable residues as solids.

The dicarboxylate salt present in the washed or unwashed solid phase is in general dissolved therefrom, for example from the filter cake, by admixing with water. For this it can be necessary to use water at a temperature that is higher than room temperature, for example even steam.

This operation can be carried out depending on the choice of process for removing insoluble constituents in the apparatus used for filtering off or washing the insoluble constituents or using further apparatus suitable for this purpose such as belt filters, centrifuges, filter presses and centrifugal disk pressure filters. If desired, the aqueous phase is intimately mixed with the insoluble constituents, for example by means of an intensive mixer, before they are separated from one another. If desired, this operation is repeated two or three times in order to maximize the yield of dicarboxylate salt obtained.

In a particularly preferred embodiment, a very concentrated aqueous solution of the dicarboxylate salt can be obtained by dissolving the dicarboxylate salt out of the solid phase in from 2 to 8, preferably 3 to 4, stages, using a dicarboxylate salt solution. This will in general concentrate the dicarboxylate salt solution used and will save energy- and cost-intensive concentrating processes such as evaporation. Preferably, the first stage is carried out with a more concentrated dicarboxylate salt solution than the second stage, the second stage with a more concentrated dicarboxylate salt solution than the third stage, etc. The last stage is in general carried out with fully demineralized water. Preference is given to using the most concentrated solution for further processing (electrochemical treatment), while the other, less concentrated solutions are stored for a subsequent wash or, if the wash is carried out as a continuous process, used at once. In general, the wash solution of the first stage contains the dicarboxylate salt in a concentration within the range from 5 to 40, preferably from 15 to 30,% by weight.

The water-soluble extract, or the combined water-soluble extracts, can then be subjected to a distillation with or without reduced pressure in order that any residual alcohols and/or other volatile organic substances present therein may ideally be removed. Furthermore, it can be advantageous to concentrate the aqueous solution prior to the electrochemical treatment by removing the water by distillation.

The insoluble constituents optionally obtained after the dicarboxylate salt has been dissolved can if desired be further used as fillers when dry.

Impurities that interfere with the electrochemical treatment such as alkaline earth metal cations, silicate and polyphosphate anions or high molecular weight organic amine compounds can advantageously be removed from the aqueous solutions freed of insolubles and diamines and comprising essentially the dicarboxylate salts, by treating these solutions with adsorbents and/or suitable precipitants.

The adsorbents used are preferably activated carbon, anthracite, calcined coke and macroporous organic ion exchangers and also further inorganic adsorbents. Suitable precipitants include carbonates of alkali metals and/or ammonium carbonates.

From observations to date the manner of the electrochemical treatment has in principle no bearing on the success of the process of the invention.

The electrochemical treatment may for example take one of the following forms (a) to (f):

(a) In this version the splitting of the dicarboxylate salt into the corresponding dicarboxylic acid and the corresponding base can be carried out in a two-part electrodialysis cell using bipolar membranes. In general, the electrodialysis cell has between the anode and the cathode from 1 to 200, preferably from 20 to 70, electrodialysis units separated from one another by bipolar membranes. The bipolar membranes are separated from one another by cation exchange membranes, so that an electrodialysis unit has the following structure: bipolar membrane (anode side)—anolyte compartment—cation exchange membrane—catolyte compartment—bipolar membrane (cathode side). The individual electrodialysis units are preferably electrically connected in series.

In this version it is advantageous to feed the aqueous dicarboxylate salt solution into the anolyte compartment. In the electric field of an applied direct voltage the alkali metal cations generally migrate through the cation exchange membrane into the catolyte compartment. The hydroxyl anions required for compensating the separated charges are formed by the dissociation of the water in the bipolar membranes on the cathode side. In this way the corresponding alkali metal hydroxide solution collects in the catolyte compartment. In the anolyte compartment the dicarboxylate anion can combine with the hydrogen ions from the bipolar membrane on the anode side to form the free dicarboxylic acid.

It is advantageous to feed the dicarboxylate salt solution into the anolyte compartments in parallel. The product streams from the anolyte compartments, containing the free acid and unconverted dicarboxylate salt, and the product streams from the catolyte compartments are advantageously combined with one another. The free dicarboxylic acid is in general obtained by crystallization from the combined product streams from the anolyte compartment without coprecipitation of the corresponding dicarboxylate salt, which is preferably subjected again to the electrodialysis process.

The electrodialysis process can be carried out not only continuously but also batchwise. A preferred form of the continuous process involving a plurality of electrodialysis cells comprises dividing the total conversion between from 2 to 20, preferably from 4 to 6, electrodialysis cells and achieving only partial conversion in each electrodialysis cell.

It is particularly advantageous here to guide the flows in countercurrent. The outflow from an anolyte compartment forms the inflow into the next anolyte compartment, etc., so that the outflow from the last anolyte compartment is rich in dicarboxylic acid and lean in dicarboxylate salt. The outflow from the last catolyte compartment, containing a low concentration of alkali metal hydroxide, forms the inflow into the last but one catolyte compartment, etc., so that the first unit has a high concentration of dicarboxylate salt in the anolyte compartment and a high concentration of alkali metal hydroxide in the catolyte compartment. The result is that the alkali metal hydroxide concentration differences in anolyte and catolyte compartments are small within a unit. This ultimately leads in general to an energy saving due to a higher current yield and on average to lower cell voltages.

The current densities are in general within the range from 0.1 to 2, preferably from 0.5 to 1.0, $kA/m^2$. The cell voltage is in general from 3 to 8 V per electrodialysis unit.

The pH is in general within the range from 2 to 10 in the anolyte compartments and within the range greater than 13 in the catolyte compartments.

The compartment width is in general from 0.2 to 5, preferably from 0.5 to 1, mm.

The electrodialysis temperature is in general within the range from 40 to 110° C., preferably from 65 to 90° C.

The inflow and outflow velocities are in general within the range from 0.05 to 0.2 m/sec.

The concentration of dicarboxylate salt used is in general from 5 to 40% by weight, preferably from 10 to 20% by weight.

If desired, the conductivity in the anolyte system can be increased by adding salts or acids such as sodium sulfate or sulfuric acid. Substances of this type are in general added within the range from 0.1 to 10% by weight, preferably from 1 to 6% by weight, based on the total weight of the solution present in the anolyte compartment.

To the catolyte compartment it is advantageous to add the substances which are obtained in the course of the operation, preferably the corresponding alkali metal hydroxide such as sodium hydroxide or potassium hydroxide, preferably sodium hydroxide.

The inflow into the catolyte compartment generally comprises fully demineralized water, but at the beginning it is preferable to employ the from 1 to 25, preferably from 5 to 10,% strength by weight alkali metal hydroxide solution formed in the course of the electrodialysis.

(b) A three-part electrodialysis cell with bipolar membranes has the advantage over the procedure described under (a) that the feed materials need not be very pure. Furthermore, in general, significantly lower salt contents are obtained not only in the dicarboxylic acid solution obtained but also in the corresponding alkali metal hydroxide solution.

The three-compartment system contains not only a cation exchange membrane but also an anion exchange membrane, so that the structure of an electrodialysis unit is as follows: bipolar membrane (anode side)—anolyte compartment—anion exchange membrane—center compartment—cation exchange membrane—catolyte compartment—bipolar membrane (cathode side).

The dicarboxylate salt solution is advantageously introduced into the center compartment. Under the influence of a direct current electric field the dicarboxylate anions generally migrate through the anion exchange membrane into the anolyte compartment, where they can combine with the hydrogen ions present there to form the free acid. Apart from selectivity losses at the anion exchange membrane the free acid can be withdrawn from the anolyte compartment devoid of salt. As in (a) the catolyte compartment yields the alkali metal hydroxide solution. The outflow from the center compartment, still containing residual quantities of dicarboxylate salt, can be disposed of or advantageously added to the feed of the dicarboxylate salt dissolution stage (where the dicarboxylate salt obtained in the cracking is dissolved). Again as in (a) the flows can be guided countercurrently in order to increase the current yield.

To increase the conductivity the anolyte compartment can have added to it for example an oxoacid such as sulfuric acid, phosphoric acid or nitric acid.

The catolyte compartment can advantageously have added to it the substances which are obtained in the course of the operation, preferably the corresponding alkali metal hydroxide such as sodium hydroxide or potassium hydroxide, preferably sodium hydroxide. As for the rest, the process of (b) can be carried out under the same conditions as described under (a).

(c) In principle it is also possible to use electrodialysis cells having four compartments. The layout generally resembles that of an electrodialysis cell with three compartments except that, to protect the bipolar membranes from fouling, a further ion exchange membrane, preferably a cation exchange membrane, is included. In general, an electrodialysis unit will have the following structure: bipolar membrane (anode side)—anolyte compartment—cation exchange membrane—anode-near center compartment—anion exchange membrane—cathode-near center compartment—cation exchange membrane—catolyte compartment—bipolar membrane (cathode side).

The dicarboxylate salt solution is advantageously introduced into the cathode-near center compartment with the dicarboxylic acid solution being withdrawn from the anode-near center compartment and the alkali metal hydroxide solution from the cathode compartment.

In other respects, the process of (c) can be carried out under the same conditions as described under (b).

(d) The electrochemical splitting of the dicarboxylate salt into the dicarboxylic acid and the corresponding base can be carried out under a further embodiment in a two-part membrane electrolysis cell known per se from chlor-alkali electrolysis. The membrane electrolysis cell comprises in general from 1 to 100, preferably from 20 to 70, electrolysis units grouped together in a block. In this block, the individual electrolysis units can be electrically connected in series by electrically connecting the cathode of one unit to the anode of the next unit or by using internally connected bipolar electrodes. The products generally flow in and out via separate collector lines for each compartment type. The two-part membrane electrolysis unit generally has the following structure going from the anode to the cathode: anode—anolyte compartment—cation exchange membrane—catolyte compartment—cathode.

The aqueous dicarboxylate salt solution is advantageously introduced into the anolyte compartment. Under the electric field of the applied direct voltage the alkali metal cations generally migrate through the cation exchange membrane into the catolyte compartment, where they are converted into alkali. The hydroxyl anions required for compensating the separated charges are released in the cathode reaction. The cathode reaction can be for example the cathodic evolution of hydrogen or a cathodic reduction of oxygen. The anolyte compartment generally retains the organic acid radical which combines with the hydrogen ions or their hydrated forms released in the course of the anode reaction to form the corresponding free acid. An example of an anode reaction is the anodic evolution of oxygen or the anodic oxidation of hydrogen. The anode compartment will thus have in general become leaner in the salt and richer in the free dicarboxylic acid.

The membrane electrolysis process can be carried out not only batchwise but also continuously. If it is carried out over the continuous process, one option is to divide the conversion between from 2 to 20, preferably from 4 to 6, cells and to guide the flows countercurrently (see (a)).

The dicarboxylate salt solution used, which may contain a plurality of such salts, has in general a concentration of from 1% by weight up to the saturation limit of the salt(s), preferably from 5 to 35, particularly preferably from 15 to 30,% by weight.

The current densities are in general within the range from 0.5 to 10, preferably from 1 to 4, $kA/m^2$. The cell voltage is in general from 2 to 10 V, preferably from 3 to 5 V, per membrane electrolysis unit.

The pH is in general within the range from 2 to 10, preferably from 3 to 5, in the anolyte compartment and within the range greater than 13 in the catolyte compartment.

The compartment width is in general from 0.5 to 10, preferably from 1 to 5, mm.

The temperature selected for carrying out the membrane electrolysis process is in general within the range from 50 to 110° C., preferably from 65 to 90° C.

To ensure mass transport, the compartment contents are in general recirculated either by means of pumps or through natural convection, ie. through the mammoth pump effect due to gas evolution at electrodes. The flow velocities in the compartments are in general within the range from 0.05 to 0.5, preferably from 0.1 to 0.2, m/sec.

(e) A particularly preferred embodiment is the electrochemical splitting of the dicarboxylate salts into the corresponding dicarboxylic acids and bases in a three-part membrane electrolysis cell.

The three-part membrane electrolysis unit has in general the following structure: anode—anolyte compartment—cation exchange membrane—center compartment—cation exchange membrane—catolyte compartment—cathode.

The aqueous dicarboxylate salt solution is in general introduced into the center compartment. To increase the electric conductivity in the center compartment, a mineral acid or a salt can be added to the center compartment electrolyte. Examples are sulfuric acid, nitric acid, sodium sulfate and sodium nitrate.

The center compartment generally retains the organic acid radical, which can react with the hydrogen ions liberated in the course of the anode reaction and which have migrated into the center compartment through the anode-side cation exchange membrane to form the free acid. The acid is in general removed from the center compartment system together with unconverted salt. The anolyte used can be an aqueous mineral acid such as sulfuric acid, nitric acid or hydrochloric acid, preferably sulfuric acid. The anolyte's essential function is, together with the anode-side cation exchange membrane, to protect the organic dicarboxylic acid from anodic oxidation.

As for the rest, the process of (e) can be carried out under the conditions described at (d).

(f) The electrochemical splitting of the dicarboxylate salts into the corresponding dicarboxylic acids and bases can also be carried out in a four-part membrane electrolysis cell.

The four-part membrane electrolysis unit generally has the following structure: anode—anolyte compartment—cation exchange membrane—anode-near center compartment—anion exchange membrane—cathode-near center compartment—cation exchange membrane—catolyte compartment—cathode.

The aqueous dicarboxylate salt solution is advantageously introduced into the cathode-near center compartment.

To increase the electric conductivity in the center compartment, a mineral acid or a salt such as sulfuric acid, nitric acid, sodium sulfate or sodium nitrate can be added to the center compartment electrolyte.

The acid anion generally passes from the cathode-near center compartment into the anode-near center compartment, where it reacts with hydrogen ions, which are evolved in the course of the anode reaction and pass into the anode-near center compartment through the anode-side cation exchange membrane, to form the free acid. The acid is in general withdrawn from the center compartment system in high purity. The remaining salt solution is in general withdrawn from the cathode-near center compartment and recirculated into the adipate dissolution stage in a partial stream or disposed of. The anolyte used is in general an aqueous mineral acid, preferably sulfuric acid. The anolyte's essential function, together with the anode-side cation exchange membrane, is to protect the organic acid from anodic oxidation.

As for the rest, the process of (f) can be carried out under the conditions mentioned at (d).

In the above-described alternatives the cation exchange membranes used are particularly preferably polymers based on perfluorinated olefins or copolymers of styrene and divinylbenzene containing sulfonic acid and if desired carboxyl groups as charge carriers. Very particular preference is given to using membranes that contain sulfonic acid groups only, since in general they are more resistant to fouling by multivalent cations than other membranes. Membranes of this type are known (for example Nafion® membranes of type 324). They consist of a copolymer of tetrafluoroethylene with a perfluorinated monomer that contains sulfone groups. In general they have a high chemical and thermal stability. The ion exchange membrane can be reinforced with a Teflon support fabric. It is also possible to use copolymers based on styrene and divinylbenzene.

Suitable anion exchange membranes are for example the membranes described in detail in EP-A-449,071 so no details will be given here.

The electrode materials used can be in general perforated materials, for example in the form of nets, lamellae, oval profile webs or round profile webs.

The oxygen overvoltage at the anodes is in general set at less than 400 mV within the current density range according to the invention in order that the formation of ozone or per-compounds may be prevented.

Suitable anode materials of low oxygen overvoltage are for example titanium supports with electrically conducting interlayers of borides and/or carbides and/or silicides of subgroups IV to VI such has tantalum borides, titanium borides or titanium suboxide, doped or undoped tin oxides, or tantalum and/or niobium with or without platinum metal doping, whose surface has in general been doped with electrically conducting, non-stoichiometric mixed oxides of subgroups IV to VI and metals or metal oxides of the platinum group or platinum metal compounds such as platinates. On top of these interlayers is in general the active electrode material, which preferably consists of mixed oxides of tantalum with iridium, platinum or rhodium and platinates of the type $Li_{0.3}Pt_3O_4$. To enlarge the surface area it is customary to use superficially roughened or macroporous titanium supports.

The cathodes are in general made of electrode materials having a low hydrogen overvoltage in order to avoid additional voltage losses in the membrane electrolysis or electrodialysis cell. Suitable cathodes are for example iron or nickel supports which have been surface coated with finely divided cobalt, nickel, molybdenum, tungsten, manganese, Raney metal compounds of nickel or of cobalt, nickel—or cobalt—aluminum alloys, or nickel—iron alloys or cobalt—iron alloys containing from 65 to 90% by weight of iron.

To improve selectivity and membrane life the cathode side can be equipped with cation exchange membranes containing hydroxyl ion blockers. The selectivity can be further improved by keeping the level of calcium, magnesium and aluminum ions and also the silica content in each case below 5 ppm.

The dicarboxylic acid obtained by the electrochemical treatment is in general present as an aqueous solution having a concentration within the range from 1 to 30, preferably from 4 to 30,% by weight. This solution can contain the conductivity salt, if present, in a concentration within the range from 0.05 to 15, preferably from 0.06 to 6,% by weight and the mineral acid, if present, in a concentration within the range from 0.05 to 15, preferably from 0 to 6, % by weight.

The alkali obtained according to the invention generally contains an alkali metal hydroxide in a concentration within the range from 5 to 35, preferably from 10 to 25,% by weight.

Particularly preferably, the alkali metal hydroxide solution obtained according to the invention can be recirculated or otherwise used, in which case if desired it can be concentrated beforehand in a conventional manner, for example by evaporation.

To obtain the dicarboxylic acid in pure form, it is in general crystallized out of the solution obtained according to the invention, then separated off, for example by filtration, and dried.

The dicarboxylic acid is preferably obtained from the electrodialysis or membrane electrolysis solutions by cooling or evaporation crystallization. Then the dicarboxylic acids are in general separated from the resulting suspensions, for example by filtration, decanting or centrifuging.

The cooling crystallization is customarily carried out at from 0 to 50° C., preferably at from 10 to 40° C., advantageously at pressures within the range from 1 to 100 kPa, preferably from 4 to 20 kPa.

The dicarboxylic acids obtained can be preferably obtained in a pure form by washing, for example with water or $C_1$–$C_4$-alkanols, and if desired by recrystallization. If a plurality of dicarboxylic acids are present at the same time, the individual dicarboxylic acids can be isolated in pure form by utilizing the solubility differences in a conventional manner such as fractional crystallization.

The aqueous solutions obtained by crystallization and washing can be concentrated in a conventional manner and resubjected to a crystallization, for example by adding them to as-electrodialyzed or as-electrolyzed solutions that have still to be crystallized. They can also be for example added to the solid phase obtained from the base treatment of the polymers used, or mixtures obtained therefrom.

One advantage of the process of the invention over known processes is that it eliminates the formation and disposal of salts which are customarily obtained when the dicarboxylic acids are freed from their salts by acidification. A further advantage is that even fiber-reinforced, mineral-filled and/or impact-modified molding compositions can be processed. Furthermore, the substances produced by the process of the invention, such as dicarboxylic acids, diamines and bases and also, as the case may be, glass fibers and mineral fillers, can be used for making new products.

EXAMPLE 1

Figure 1:
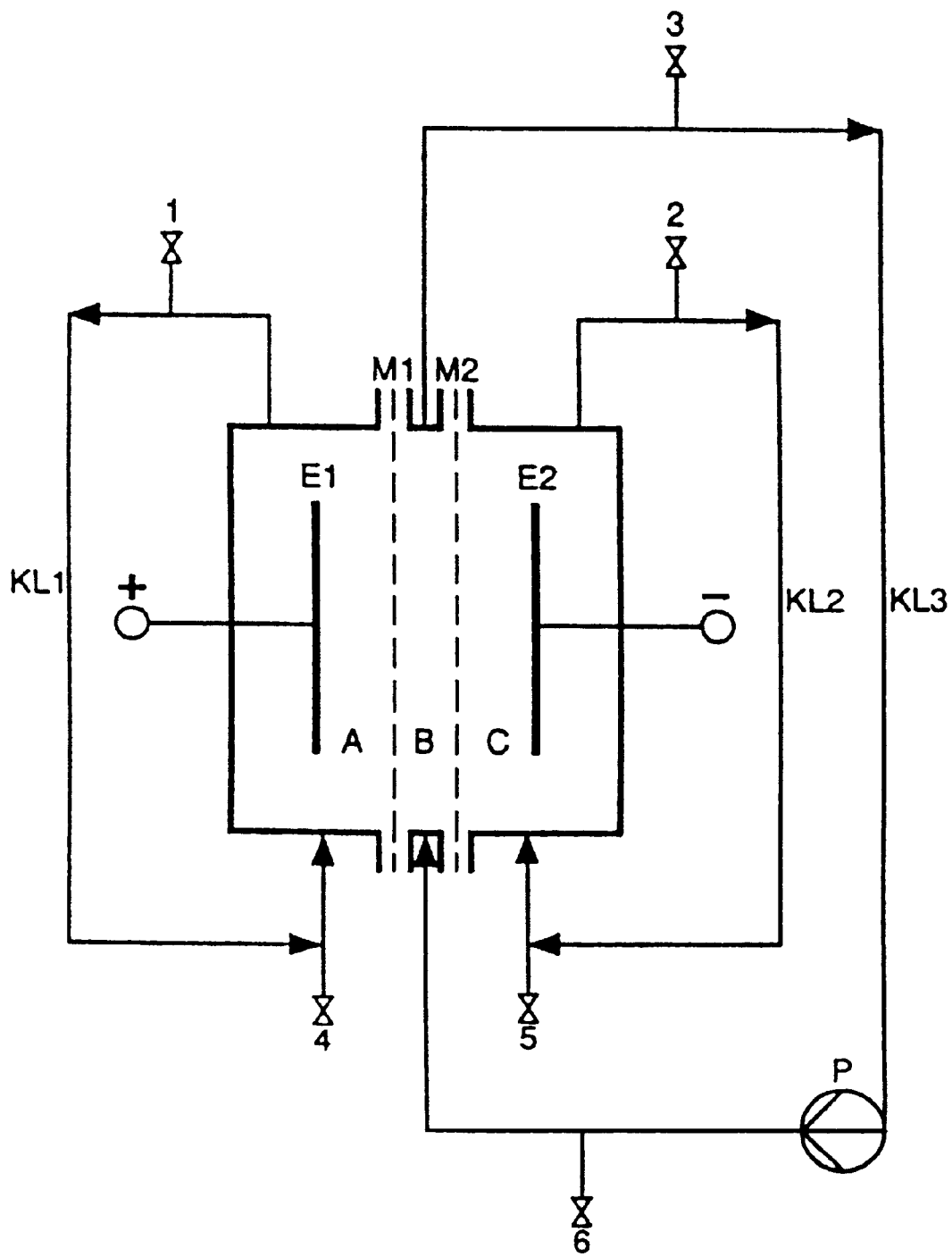
FIG. 1 depicts an apparatus for use with a preferred embodiment of the invention (see Example 4). The apparatus is a three-compartment (A, B, and C) electrolysis cell with three liquid cycles (KL1, KL2, and KL3). E1 (in compartment A) depicts an anode. E2 (in compartment C) depicts a cathode. Membranes M1 and M2 are positioned on the electrodes E1 and E2, respectively. Pump P is used to recirculate the center compartment electrolyte. The anolyte is introduced at location 1, and removed at location 4. The catolyte is introduced at location 2, and removed at location 5. The center compartment electrolyte is introduced location 3, and removed at location 6.

300 g of a nylon 66 having a viscosity number (VN)=149 (unit: 1 $cm^3$/g) (measured on a 0.5% strength by weight solution of the nylon in 96% strength by weight sulfuric acid at 25° C. in accordance with DIN 53 727) and comminuted to about 8 mm (average particle diameter) were heated together with 780 g of a 15% strength by weight solution of sodium hydroxide in methanol at 180° C. for 4 hours in a pressure vessel with stirring.

After this reaction mixture had been cooled down, the precipitated sodium adipate was filtered off, washed repeatedly with methanol and dried.

The mother filtrate and the combined methanolic wash filtrates were subjected to a fractional distillation. Initially the low boilers such as methanol were separated off at atmospheric pressure. At 128–131° C./100 mbar 142 g of hexamethylenediamine were then obtained in the form of a colorless melt.

249 g of the dried sodium adipate were then admixed with 673 g of water, so that a 27% strength by weight aqueous sodium adipate solution was obtained.

This concentrated sodium adipate solution was then admixed with 0.5 g of pulverized activated carbon per 100 ml of solution and heated to 50° C. After 1 h the activated carbon was filtered off and 80 mg of sodium carbonate per 100 g of solution were added with stirring. After 1 h the stirrer was switched off and after a further 4 h the solution was filtered. This pre-purified sodium adipate solution was then subjected to a treatment with a selective ion exchange resin (Lewatit TP 208 (from Bayer)).

EXAMPLE 2

In a pressure vessel 300 g of comminuted nylon 66 (as described in Example 1) were heated with stirring with 970 g of a 12.2% strength by weight solution of sodium hydroxide in a solvent mixture consisting of 85% by volume of methanol and 15% by volume of water, at 180° C. for 4 hours.

After the reaction mixture had been cooled down, the precipitated sodium adipate was filtered off, washed repeatedly with a total of 750 g of methanol and dried. The combined methanolic wash filtrates were reused as solvent for the hydrolysis stage.

The mother filtrate of the reaction mixture was subjected to a fractional distillation. Initially low boilers such as methanol and water were separated off under atmospheric pressure. At 128–131° C./100 mbar 138 g of hexamethylenediamine were obtained in the form of a colorless melt.

The workup of the sodium adipate to adipic acid and sodium hydroxide solution was carried out analogously to Example 1, the sodium hydroxide solution obtained in the electrolysis being concentrated to 50% by weight and reused in the splitting reaction (hydrolysis stage). This again involved heating 300 g of comminuted nylon 66 (as described in Example 1) with 232 g of 50% strength by weight sodium hydroxide solution and 730 g of the methanolic wash filtrate at 180° C. for 4 hours with stirring.

After the reaction mixture had cooled down, the precipitated sodium adipate was filtered off and repeatedly washed with a total of 750 g of methanol. The methanol used for this washing of the filter cake had been recovered pure from the rectification of the mother filtrate.
(The rest of the workup was carried out analogously to Example 1).

EXAMPLE 3

This experiment was carried out using a pigmented (with carbon black), (thermally stabilized) glass fiber-reinforced nylon 66 having a viscosity number (VN)=140 (measured in accordance with DIN 53 727, see Example 1) and a glass fiber content of 36% by weight (determination of the calcination loss of glass fiber-reinforced plastics in accordance with DIN 53 395) which had been comminuted to about 8 mm (average particle diameter). In a pressure vessel 490 g of this composite material were heated with stirring with 1180 g of a 10% strength by weight solution of sodium hydroxide in a solvent mixture consisting of 75% by volume of methanol and 25% by volume of water at 180° C. for 4 hours.

After the reaction mixture had cooled down, the precipitated sodium adipate was filtered off together with the glass fibers (and other insoluble constituents such as carbon black pigments) and repeatedly washed with methanol. The mother filtrate and the combined wash filtrates were subjected to a fractional distillation. Initially low boilers such as methanol and water were separated off at atmospheric pressure. At 128–131° C./100 mbar 140 g of hexamethylenediamine were obtained in the form of a colorless melt.

To recover the sodium adipate, the filter residue of the reaction mixture was repeatedly admixed with a total of 1000 g of water, stirred up and filtered. The combined filtrate gave a 20% strength by weight aqueous sodium adipate solution which was evaporated under atmospheric pressure to a concentration of 27% by weight of sodium adipate, methanol residues being removed as well.

The sodium adipate solution thus concentrated was then admixed with 0.5 g of pulverized activated carbon per 100 ml of solution and heated to 50° C. After 1 h the activated carbon was filtered off.
(The rest of the workup was carried out analogously to Example 1).

EXAMPLE 4

Batchwise Electrolysis in a Three-Compartment Electrolysis Cell as per Variant e)

The three-compartment electrolysis cell used was that diagrammatically depicted in FIG. 1 with three liquid cycles (KL1 to KL3). All product-contacting parts with the exception of the electrodes consisted of polypropylene, glass or quartz. The anode (E1) (in compartment (A)) was a titanium expanded-mesh anode having an area of 100 $cm^2$ and a coating suitable for oxygen evolution. The cathode (E2) (in compartment (C)) likewise had an area of 100 $cm^2$. It consisted of a chromium-nickel stainless steel (1.4571) which had been coated with a nickel network activated for hydrogen evolution. The two membranes (M1 and M2) of the type Nafion® 324 were positioned directly on the electrodes (E1 and E2, respectively) and were separated from each other by a 1 mm wide center compartment (B) with a polypropylene spacer.

The anode (KL1) and cathode (KL2) cycles were kept in natural circulation owing to the gas evolutions at the electrodes. The cycle of the center compartment (B), (KL3), was recirculated using a cycle pump (P). The flow velocity in the center compartment (B) was 0.1 m/sec.

The anolyte used comprised 1131 g of 5% strength by weight sulfuric acid introduced at location (1), the catolyte comprised 1161 g of 5% strength by weight sodium hydroxide solution introduced at location (2), and the center compartment electrolyte comprised 995 g of 27% strength by weight sodium adipate solution obtained in Example 1 to which 21 g of 96% strength by weight sulfuric acid were added so that 1015 g of a solution containing 22% by weight of sodium adipate, 2.9% by weight of adipic acid and 2.8% by weight of sodium sulfate were introduced at location (3).

A temperature of 80° C., atmospheric pressure, a current density of 3.0 $kA/m^2$, a cell voltage of 4.0 V (at the beginning) and 5.3 V (at the end of the run) produced with a current yield of 83% and after a reaction time of 2 h 26 min the following electrolytes:
anolyte (removed at location (4)): 729 g of 6.9% strength by weight sulfuric acid,
catolyte (removed at location (5)): 1294 g of 10.9% strength by weight sodium hydroxide solution,
center compartment electrolyte (removed at location (6)): 904 g of a solution containing 20.4% by weight of adipic acid, 1.2% by weight of sodium adipate and 3.2% by weight of sodium sulfate.

Batchwise Crystallization 900 g of the center compartment electrolyte solution thus obtained were introduced at 80° C. into a vacuum vessel with reflux condenser and then cooled down over 100 min to 10° C. (by continuously reducing the internal pressure (absolute) from 1013 mbar to 12 mbar). The resulting adipic acid crystals were then separated off by means of a vacuum nutsche at a filtration pressure of 450 mbar and washed with 700 g of water which had a temperature close to 0° C. The crystalline product thus washed was then dissolved in 420 g of water, giving a 30% strength by weight adipic acid solution. Then the crystallization process was repeated. Drying the crystalline product obtained in the second crystallization process at 80° C. and 100 mbar (absolute) left 175 g of adipic acid having a purity of 99.8% and an ash content of less than 8 ppm.

Continuous Crystallization

Example 4 was repeated except that the adipic acid was purified by continuous crystallization. For this two vacuum vessels (0.75 l nominal capacity, with stirrer) were connected in series. The absolute pressure of the first stage (vessel 1) was 95 mbar (corresponding to a boiling temperature of the adipate solution used of 45° C.), the absolute pressure of the second stage was 12 mbar (corresponding to a boiling temperature of the adipate solution used of 10° C). The liquid level was kept constant in the two vessels by using a membrane metering pump to pump 0.75 kg/h of adipate solution continuously into the first vacuum vessel and decompressing under a blanket of liquid. A level control valve was used to likewise introduce 0.75 kg/h of the solution contained in the first vacuum vessel into the second vacuum vessel, the solution transported from the first into the second vacuum vessel likewise being decompressed "dipped". A charge (900 g) of the adipic acid crystallized out of the second vessel was separated off by means of a vacuum nutsche at a filtration pressure of 450 mbar and washed with 700 g of water which had a temperature close to 0° C. The crystalline product thus washed was then dissolved in 420 g of water, giving a 30% strength by weight adipic acid solution. Then the crystallization process was repeated. Drying the crystalline product obtained in the second crystallization process at 80° C. and 100 mbar (absolute) gave 175 g of adipic acid having a purity of 99.8% and an ash content of less than 8 ppm.

EXAMPLE 5
Batchwise Electrolysis in a Four-Compartment Electrolysis Cell as per Variant f)

Figure 2:
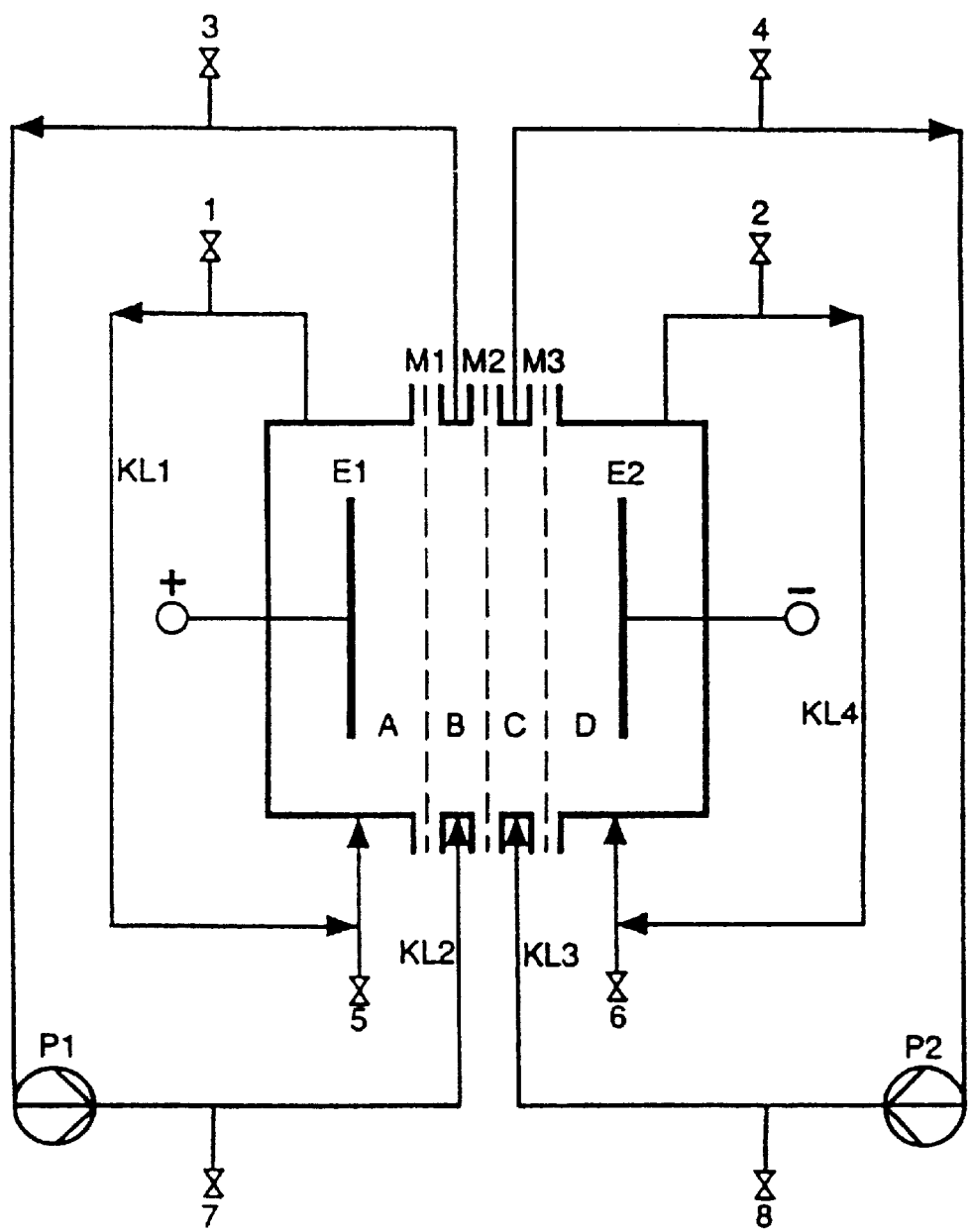
FIG. 2 also depicts an apparatus for use with a preferred embodiment of the invention (see Example 5). The apparatus is a four-compartment (A, B, C, and D) electrolysis cell with four liquid cycles (KL1, KL2, KL3, and KL4). E1 (in compartment A) depicts an anode. E2 (in compartment D) depicts a cathode. Membranes M1 and M3 are positioned on the electrodes E1 and E2, respectively. Membrane M2 is positioned between the two center compartments B and C. Pumps P1 and P2 are used to recirculate the electrolyte of center compartments B and C, respectively. The anolyte is introduced at location 1, and removed at location 5. The catolyte is introduced at location 2, and removed at location 6. The electrolyte of center compartment B is introduced location 3, and removed at location 7. The electrolyte of center compartment C is introduced at location 4, and removed at location 8.

The four-compartment electrolysis cell used is diagrammatically depicted in FIG. 2 with four liquid cycles (KL1 to KL4). All product-contacting parts with the exception of the electrodes consisted of polypropylene, glass or quartz. Anode (E1) (in compartment (A)) was a titanium expanded-mesh anode having an area of 100 cm² and a coating suitable for oxygen evolution. Cathode (E2) (in compartment (D)) likewise had an area of 100 cm². It consisted of chromium—nickel stainless steel (1.4571) which had been coated with a nickel network activated for hydrogen evolution. The two electrode-near cation exchange membranes (M1 and M3) of the type Nafion® 324 were positioned directly on the electrodes (E1 and E2 respectively) and were separated by two center compartments, (B) and (C), each 1 mm in width, with a centrally disposed anion exchange membrane (M2) of the type Tokuyama Sodas® AMH. The center compartments, (B) and (C), were provided with two polypropylene spacers which served to keep the flow channel free and to prevent direct contact between the membranes.

The anode (KL1) and cathode (KL4) cycles were kept in natural circulation owing to the gas evolutions at the electrodes. The cycles of the center compartments (B) and (C), (KL2) and (KL3), were recirculated using the cycle pumps (P1) and (P2). The flow velocities in the center compartments (B) and (C) were in each case 0.1 m/sec.

The anolyte used comprised 1108 g of 5.1% strength by weight sulfuric acid introduced at location (1), the catolyte comprised 1101 g of 4% strength by weight sodium hydroxide solution introduced at location (2), the electrolyte of the anode-near center compartment (B) comprised 1097 g of 2.1% strength by weight sulfuric acid introduced at location (3), and the electrolyte of the cathode-near center compartment (C) comprised 1505 g of 27% strength by weight sodium adipate solution obtained in Example 2 introduced at location (4).

During the reaction a total of 900 g of water was additionally introduced into the cathode-near center compartment (C).

A temperature of 80° C., atmospheric pressure, a current density of 3.0 kA/m², a cell voltage of 7.0 V (at the beginning) and 8.7 V (at the end of the run) produced with a current yield of 75% and after a reaction time of 5 h, during which the pH in the cathode-near center compartment (C) was within the range from 10 to 12, the following electrolytes:

anolyte (removed at location (5)): 793 g of 7.1% strength by weight sulfuric acid, catolyte (removed at location (6)): 1584 g of 13.3% by strength weight sodium hydroxide solution, product of the anode-near center compartment (B) (removed at location (7)): 2034 g of a solution containing 15.1% by weight of adipic acid, 1.1% by weight of sulfuric acid, product of the cathode-near center compartment (C) (removed at location (8)): 1061 g of a 1.4% strength by weight sodium adipate solution.

EXAMPLE 6
Batchwise Electrolysis in a Membrane Stack Cell as per Variant b)

Figure 3:
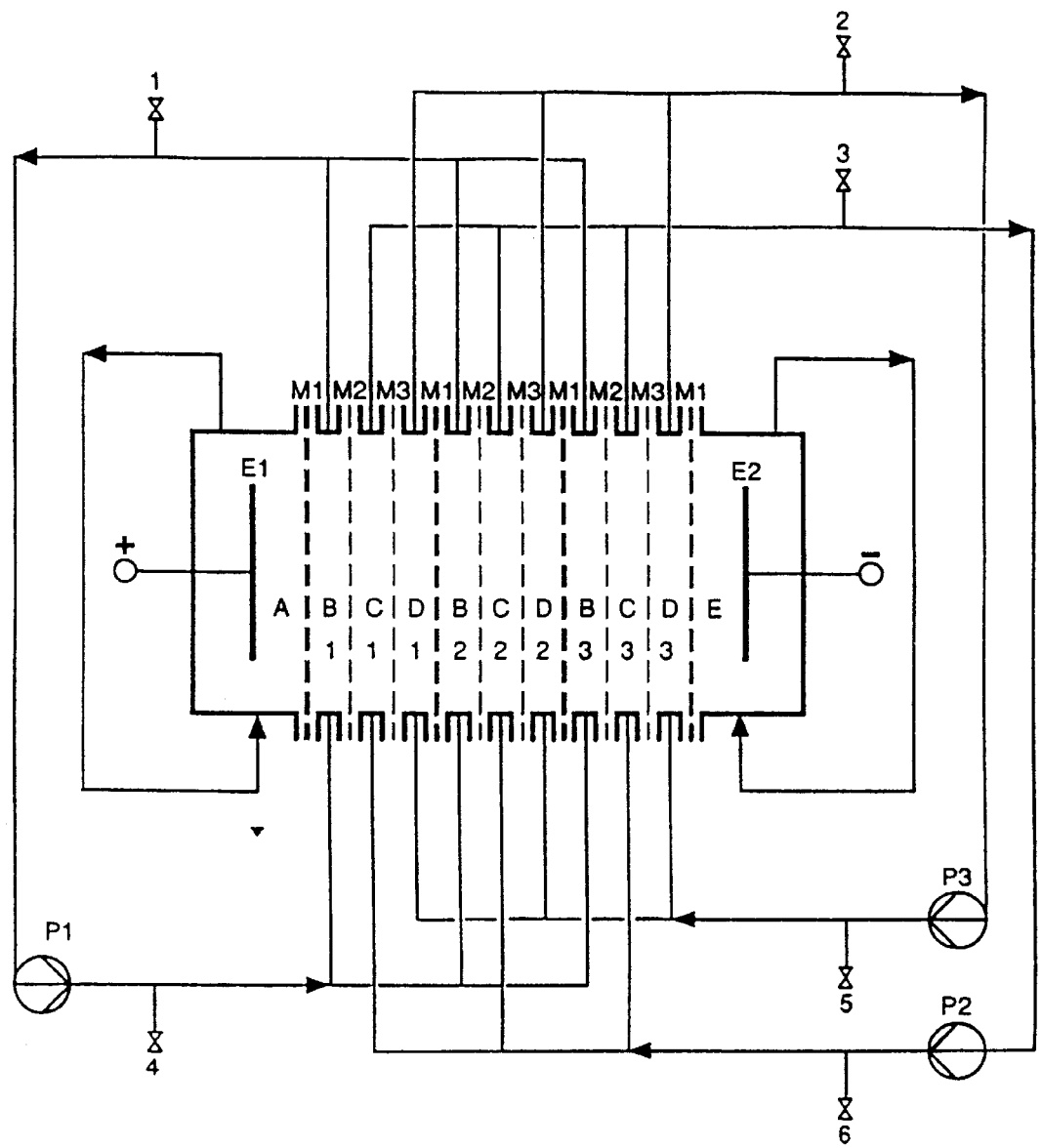
FIG. 3 again depicts an apparatus for use with a preferred embodiment of the invention (see Example 6). The apparatus is a membrane stack electrolysis cell with eleven compartments (A, B1, B2, B3, C1, C2, C3, D1, D2, D3, and E). E1 (in compartment A) depicts an anode. E2 (in compartment E) depicts a cathode. The compartments A and B1, D1, and B2, D2 and B3, and also D3 and E are separated by bipolar membranes M1. The compartments B1 and C1, B2 and C2, and also B3 and C3 are separated by anion exchange membranes M2. The compartments C1 and D1, C2 and D2, and also C3 and D3 are separated by cation exchange membranes M3. Pumps P1, P2, and P3 are used to recirculate the electrolyte of the center compartments. The electrolyte of center compartments B1, B2, and B3 is introduced location 1, and removed at location 4. The electrolyte of center compartments C1, C2, and C3 is introduced at location 3, and removed at location 6. The electrolyte of center compartments D1, D2, and D3 is introduced at location 2, and removed at location 5.

The membrane stack cell used is diagrammatically depicted in FIG. 3 with three liquid cycles (KL1 to KL3). All product-contacting parts with the exception of the electrodes consisted of polypropylene, glass or polytetrafluoroethylene. Anode (E1) (in compartment (A)) was a titanium expanded-mesh anode having an area of 320 cm² and a coating suitable for oxygen evolution. Cathode (E2) (in compartment (D)) likewise had an area of 320 cm². It consisted of a chromium—nickel stainless steel (1.4571) which had been coated with a nickel network activated for hydrogen evolution.

The compartments (A) and (B1), (D1) and (B2), (D2) and (B3) and also (D3) and E were in each case separated from each other by a bipolar membrane (from DE-A 40 26 154). The compartments (B1) and (C1), (B2) and (C2) and also (B3) and (C3) were kept apart from each other by anion exchange membranes (Tokuyama® Soda AMX). The compartments (C1) and (D1), (C2) and (D2) and also (C3) and (D3) were kept apart from each other by cation exchange membranes (Tokuyama® Soda CMX). The membrane spacings were in each case 0.5 mm.

All liquid cycles with the exception of those of the anode (A) and cathode (E) compartments were recirculated by means of cycle pumps, (P1) to (P3), the flow velocity being in each case 0.1 m/sec.

The electrolyte used in the acid medium comprised 10000 g of 1.5% strength by weight sulfuric acid introduced at location (1), the electrolyte in the basic medium comprised 5000 g of 1% strength by weight sodium hydroxide solution introduced at location (2) and the center compartment electrolyte comprised 5000 g of 20% strength by weight sodium adipate solution (obtained by diluting the 27% strength by weight solution obtained) in Example 3 introduced at location (3).

A temperature of 55° C., atmospheric pressure, a current density of 0.31 kA/m², a cell voltage of 13 V (on average) produced with a current yield of 70% and after a reaction time of 13 h the following electrolytes:

dialysis product (removed at location (4)): 11555 g of 6.4% strength by weight adipic acid which additionally contained 1.3% by weight of sulfuric acid, "basic" electrolyte (removed at location (5)): 6597 g of 6.9% strength by weight sodium hydroxide solution, "depleted" center compartment electrolyte (removed at location (6)): a 1.8% strength by weight solution of sodium adipate.

We claim:
1. A process for the simultaneous production of adipic acid and hexamethylene diamine from
a) polymers based on polyamides of adipic acid or its derivatives with hexamethylene diamine, or
b) compositions containing such polymers, wherein such polymers are converted into their monomeric constituents, which process comprises:
    treating the polymers or compositions containing the polymers with a base in an alcoholic medium con- taining 5 to 40% by weight of water, separating off the hexamethylene diamine, and converting the formed adipic acid salt electrochemically into adipic acid and its corresponding base in a three-part membrane electrolysis cell having the following general structure: anode, anolyte compartment, cation exchange membrane, center compartment, cation exchange membrane, catolyte compartment, cathode, and whereby the aqueous adipic acid salt solution is introduced into the center compartment in the presence of a mineral acid or a salt, yielding a solution consisting essentially of adipic acid and a solution consisting essentially of an alkali metal hydroxide.

2. A process as defined in claim 1, wherein the electrochemical conversion is carried out at temperature within the range of from 65 to 90° C.

3. A process as defined in claim 1, wherein the electrochemical conversion is carried out at a temperature within the range of from 40 to 110° C.

4. A process as defined in claim 1, wherein the adipic acid is crystallized out from their solutions obtained by the electrochemical treatment.

5. A process as defined in claim 1, wherein the base obtained in the electrochemical treatment is used to split the polymers into their monomeric constituents.

* * * * *